United States Patent [19]

Brunnett

[11] Patent Number: 4,791,934

[45] Date of Patent: Dec. 20, 1988

[54] COMPUTER TOMOGRAPHY ASSISTED STEREOTACTIC SURGERY SYSTEM AND METHOD

[75] Inventor: Carl J. Brunnett, Willoughby, Ohio

[73] Assignee: Picker International, Inc., Highland Heights, Ohio

[21] Appl. No.: 894,317

[22] Filed: Aug. 7, 1986

[51] Int. Cl.[4] ............................................. A61B 6/00
[52] U.S. Cl. .............................. 128/653; 128/303 B; 378/20; 378/205
[58] Field of Search ................... 128/653, 303 B, 659; 378/20, 205

[56] References Cited

U.S. PATENT DOCUMENTS

| | | | |
|---|---|---|---|
| 3,720,817 | 3/1973 | Dinwiddie | 235/151.11 |
| 4,118,631 | 10/1978 | Froggatt | 250/492 R |
| 4,197,855 | 4/1980 | Lewin | 128/653 |
| 4,216,526 | 8/1980 | Karowski | 364/414 |
| 4,281,382 | 7/1981 | Knoll et al. | 364/414 |
| 4,341,220 | 7/1982 | Perry | 128/630 |
| 4,360,028 | 11/1982 | Barbier | 128/659 |
| 4,365,341 | 12/1982 | Lam | 378/205 |
| 4,384,209 | 5/1983 | Wagner et al. | 378/14 |
| 4,386,405 | 5/1983 | Lewin et al. | 364/415 |
| 4,472,822 | 9/1984 | Swift | 378/146 |
| 4,533,947 | 8/1985 | Smith | 378/901 |
| 4,583,538 | 4/1986 | Onik et al. | 128/303 B |
| 4,617,925 | 10/1986 | Laitinen | 128/303 B |
| 4,671,256 | 6/1987 | Lemelson | 128/659 |

*Primary Examiner*—Ruth S. Smith
*Attorney, Agent, or Firm*—Fay, Sharpe, Beall, Fagan, Minnich & McKee

[57] ABSTRACT

Diagnostic mapping data representing a series of planar slices through a patient are generated by a CT or other multi-plane scanner (A) and stored in an image memory (32). To free the CT or other scanner for other patients, the mapping data and patient are transferred to a second location. At the second location, the patient is restrained in a digital radiographic imaging apparatus (B) in which data representing a shadowgraphic image is generated and stored in a reference memory (60). The transferred mapping data is stored in a second image memory (32') at the second site. A shadowgraphic image synthesizer (70) synthesizes an analogous shadowgraphic image from the diagnostic mapping data in the second image memory taken relative to a selected spatial position and angular orientation. The reference and synthesized shadowgraphic images are superimposed or otherwise concurrently displayed on a video display (64). The spatial position and angular orientation from which the synthesized image is projected are adjusted until an optimal match between the superimposed images is achieved. In this manner, the current actual position of the patient and the diagnostic data in the second image memory are brought into registration. From images representing slices through the patient reconstructed from data in the image memory, the physician plans a point of entry and path through the patient which a surgical instrument (100) is to follow. A surgical instrument guide (90) is positioned such that the surgical instrument enters the patient at the coordinates at the selected point of entry and follows the selected path.

17 Claims, 2 Drawing Sheets

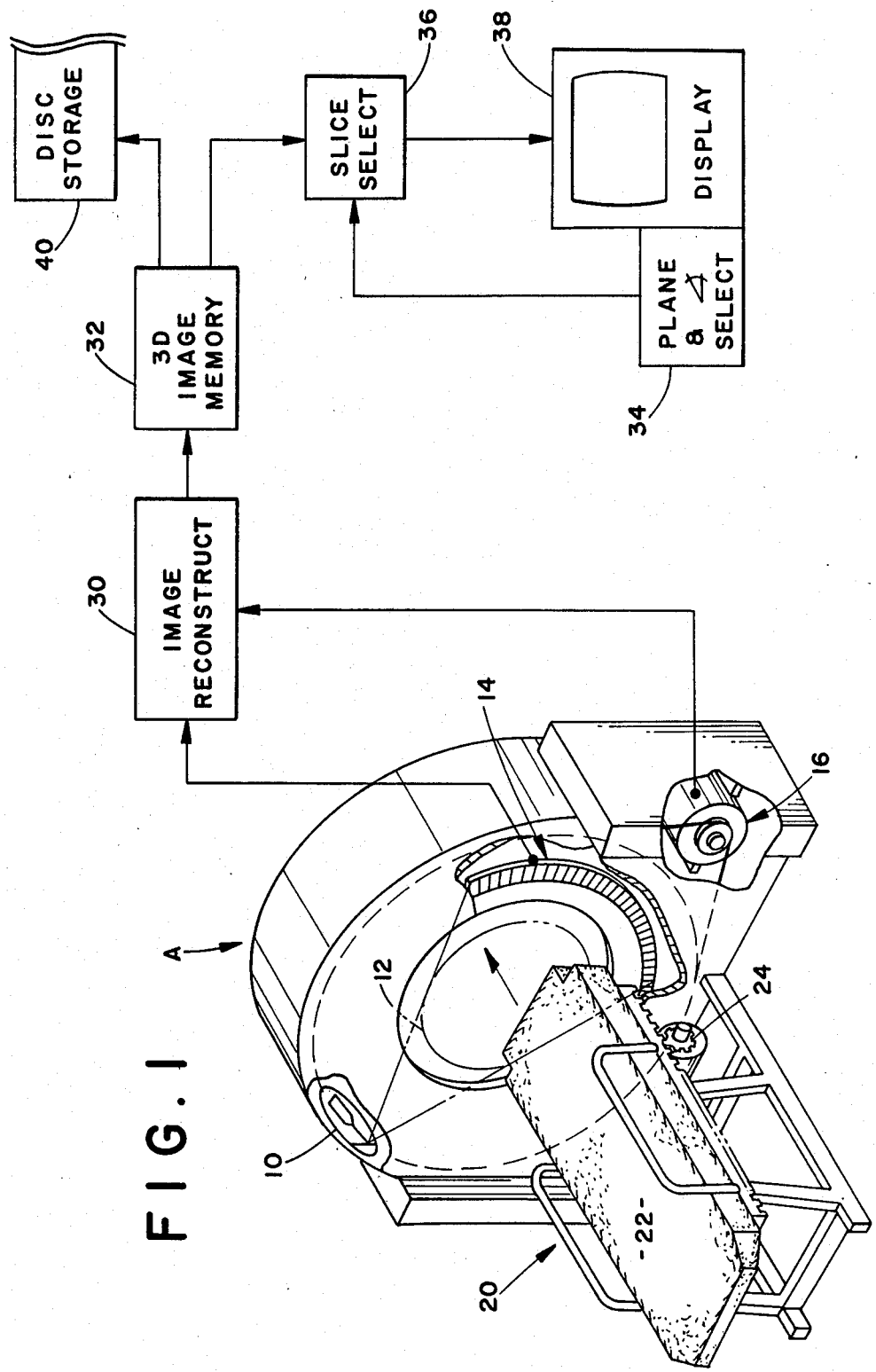

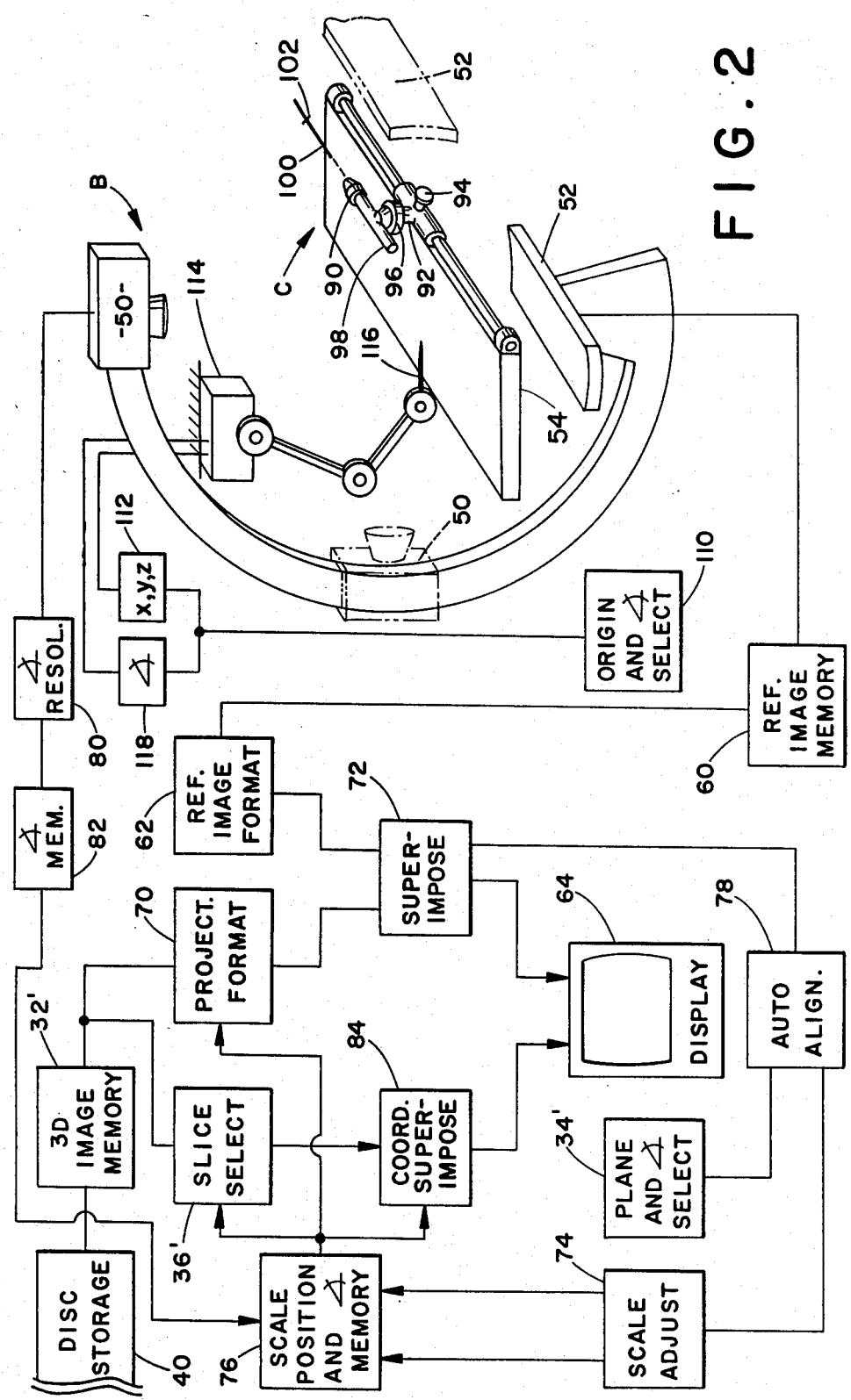

4,791,934

COMPUTER TOMOGRAPHY ASSISTED STEREOTACTIC SURGERY SYSTEM AND METHOD

BACKGROUND OF THE INVENTION

The present invention relates to the art of non-invasive examination and internal imaging. It finds particular application in combination with stereotactic surgical procedures and will be described with particular reference thereto. However, it is to be appreciated that the present invention may find other applications in which it is advantageous to orient a patient or examined object relative to images or other representations from previously collected data.

Heretofore, computed tomography scanning has been utilized to assist in various invasive clinical procedures, such as biopsies, the drainage of abscesses, placement of radiation implants, orthopedic pin placement, contrast injections, and the like. In one prior art procedure, the patient was tightly strapped to a patient table mounted on a position control structure for controlledly indexing the patient table through the imaging region of a CT scanner. Based on the reconstructed images from a plurality of planar CT scans, a path for insertion of the needle or probe was determined. Without moving the patient relative to the patient table, the patient table was shifted a preselected precise distance from the imaging region of the CT scanner. The shifting was necessary to provide ready surgical access to the patient without interference from the scanner structure. This shifting of the patient table caused a precisely known offset between the image data and the region of interest of the patient. A guide structure was positioned relative to the patient at the appropriate position and angle to direct a needle or probe through a selected point of entry and along the selected path.

After positioning the needle in the guide, the patient table was shifted such that the region of the patient of interest, the guide, and the needle were repositioned in the examination zone of the CT scanner. More CT scans were made to check the accuracy of the needle positioning relative to the selected path. If necessary, the position or angular orientation of the needle could be adjusted and additional scans taken until an acceptable alignment was achieved. Thereafter, the needle was inserted manually into the patient.

One of the drawbacks of this procedure is that it consumed excessive amounts of expensive, computed tomography scanner time. Because the patient had to be kept at precisely known distances relative to the scanner, the surgery was performed on the scanner associated patient table in the CT scanner room. During the surgery, the scanner was unavailable for performing scanning functions on other patients.

To increase the efficiency of CT scanner utilization, stereotactic fixtures have been developed for performing head and brain surgery remote from the CT scanner. The fixture was rigidly attached to the patient skull prior to the CT scan such that a fixed orientation between the fixture and the skull was maintained even as the patient moved. Reference marks on the fixture provided corresponding reference marks on the resultant images which indicated the relative position and orientation of the fixture and the images.

Thereafter, the patient, with the stereotactic device remaining attached to the skull, was removed to a separate surgical facility freeing the CT scanner for use by other patients. By studying the various images, the doctor planned and calculated an appropriate entry point and path for the needle or probe to follow. Because the relative position of the fixture and the interior head tissue remained fixed, probe guides and distance limiting structures could be selectively positioned on the stereotactic fixture such that the probe or needle would follow the calculated path. See for example U.S. Pat. No. 4,341,220, issued July 27, 1982 to Perry.

One of the drawbacks of the stereotactic fixtures is that their use was limited to areas of the body in which the fixture could be rigidly attached to bone tissue, e.g. the skull. Another drawback to stereotactic fixtures is that they must remain attached between the CT scan and the surgery. The stereotactic fixture could not be reattached with sufficient accuracy to assure the safety of most surgical procedures. For on-going surgical treatment, it was necessary that the fixture be reattached and a new CT scan conducted before each surgical procedure. The repetitive CT scans not only used large amounts of scanner time, but also subjected the patient to numerous doses of radiation.

The present invention provides a new and improved method and apparatus which enables the CT scan data to be realigned with the patient at a subsequent time and a remote location.

SUMMARY OF THE INVENTION

In accordance with a first aspect of the present invention, a method is provided for precisely locating an internal region of interest in advance of a clinical procedure. At a first site, a series of planar scans are conducted and a map of the internal structure of the subject is obtained therefrom. The patient is moved to a second site at which the invasive procedure is to be performed. At the second site, the patient is again examined but with a different, second non-invasive imaging technique to generate an image with a known spatial relationship to the patient. An image most nearly corresponding to the second technique image is generated from the internal structure map. The two images are compared to obtain an indication of the relative spatial orientation and position between the patient and the map. In this manner, the map of at least a portion of the internal structure of interest may be realigned with the actual spatial position and orientation of the corresponding internal structure of the patient.

In accordance with a more limited aspect of the invention, the image generated by the second imaging technique is a two-dimensional shadowgraph.

In accordance with another aspect of the present invention, an apparatus is provided for imaging a region of interest in advance of an invasive procedure. A scanning means is provided for scanning a series of planes of the subject and generating a map or image data indicative thereof. At least one image generating means is provided for generating a selected image from the mapping. At least one display means is provided for displaying the selected image. In this manner, a doctor can examine selected planes through a region of interest to select a path through the patient for a biopsy needle or the like. A different imaging means is provided for generating at least one two-dimensional reference image of a patient through the region of interest such that the two-dimensional image and the patient have a known spatial position and orientation relationship relative to each other. Means are provided for generating an analogous two-dimensional image from the map such that the spatial position and orientation of the map can be coordinated and aligned with a reference image, hence the patient. In this manner, the entry points and surgical paths selected on the images displayed on the display means can be coordinated with corresponding physical locations and orientations of the patient.

One advantage of the present invention is that it improves the efficiency of the utilization of CT scanners, magnetic resonance imaging, and other multi-planar imaging equipment.

Another advantage of the present invention is that it enables multi-planar image data to be utilized at subsequent times to assist in surgical procedures.

Yet another advantage of the present invention is that it facilitates the registration of multi-planar and other image data with the current spatial position and orientation of the patient.

Still further advantages of the present invention will become apparent to those of ordinary skill in the art upon reading and understanding the following detailed description of the preferred embodiments.

BRIEF DESCRIPTION OF THE DRAWINGS

The invention may take form in various steps and arrangements of steps and various components and arrangements of components. The drawings are only for purposes of illustrating a preferred embodiment of the invention and are not to be construed as limiting it. Wherein the figures show:

FIG. 1 is a diagrammatic view of a multi-planar slice imaging station;

FIG. 2 is a diagrammatic view of an apparatus at a surgical station for bringing the multi-planar slice image data into registration with the patient's current spatial position and orientation.

DETAILED DESCRIPTION OF THE PREFERRED EMBODIMENT

A detailed non-invasive examination of the patient or subject is made, preferably with a multi-slice imager A at an examination station or room, FIG. 1. Commonly, the examination results in electronic mapping data which represents a series of planar slices through the patient, a three dimensional region of the patient, or the like. Although the embodiment of FIG. 1 illustrates a computed tomography or CT scanner, it is to be appreciated that magnetic resonance and other non-invasive images may also be utilized.

The mapping data is transferred to a second site, specifically a surgical operating theater or station, FIG. 2. At the second site, the patient is examined with a second imaging device B, preferably an imaging device which generates an electronic data representing a two dimensional shadowgraphic projection at selectable angles through the patient. Analogous shadowgraphic projections or other images are synthesized or reconstructed from the mapping data from the first imager A which are compared with reference image representations from the second imager B. The shadowgraphic image synthesized from the mapping data of the first imager is adjusted until it is brought into registration with the reference images. Stereotactic surgical equipment or guides C are mounted at selectable positions and angular orientations relative to the second imager. The stereotactic surgical equipment is readily positioned relative to the patient to direct invasive surgical devices along paths selected from the mapping or first imager data.

With particular reference to FIG. 1, the first multi-slice imager A of the preferred embodiment includes an X-ray source 10 which directs a fan beam of penetrating radiation through a scan circle 12 before impinging upon an arc of radiation detectors 14. A rotating means 16 rotates at least the source of radiation 10 around the scan circle to irradiate a patient positioned therein from a plurality of directions. Magnetic resonance and other imagers are also contemplated.

A patient table or couch 20 is mounted in association with the scanner for selectively disposing a patient within the scan circle. A top 22 of the patient table and the patient thereon are selectively moved or indexed along a path transverse to the fan beam by a patient moving or indexing means 24.

As the radiation source 10 rotates around the scan circle, an image reconstruction means 30 reconstructs the data collected by each of a plurality of detectors 14 into mapping data representative of planar slices of the patient positioned within the scan circle. The slice data is stored in a three dimensional or multi-slice memory 32. The indexing means 24 then indexes the patient an incremental distance and mapping data representing additional planar slices through the patient are generated, reconstructed, and stored in the multi-slice memory 32. This process is repeated until a plurality or series of slices have been examined and the corresponding mapping data stored in the multi-slice memory 32. Conceptually, the multi-slice memory can be pictured as a three dimensional array of cubic cells, each cell storing a number which designates the relative gray scale of a corresponding pixel of a reconstructed image. Each slice corresponds to one plane of cells and adjoins the plane of cells corresponding to the slice taken to either side thereof. It is to be appreciated, however, that the resolution within each plane may differ from the inter-planar spacing, i.e. the cells may, in some scanners, need to be conceptualized as being more of a rectangular prism than a cube.

A physician or operator panel includes a plane and angle selection means 34 on which any one of the available planes may be selected for display. As is conventional in the art, a plane at any angle or orientation through the multi-sliced diagnostic image data may be selected. An image formatting or slice select means 36 performs the appropriate geometrical calculations to determine which cubes or rectangular data prisms are intersected by the selected plane. The image format means then addresses the appropriate memory addresses of the image memory 32 to extract the appropriate mapping data or gray scale numbers to format an image for display by a display means 38. Where appropriate, the image format means may perform a weighted averaging or interpolation of data form adjacent cells where the selected plane passes between adjacent cells or off center through one of the cells.

The data from the image memory is transferred to a residual storage means 40. The residual storage means may be a central data processing area of the hospital facility, a multi-hospital computer network, or a readily transportable memory medium such as a disk or tape. The readily transported tape or disc may be recorded at the patient site or at central processing. The physician may view the various imaged planes at the examination site or may call up the data at a remote viewing site, such as the physician's office or a viewing room, to make a more detailed examination of the data while freeing up the imaging apparatus. The remote viewing site includes at least a multi-slice memory which is loaded from the tape or disc, plane and angle selection means, an image formatting means, one or more video display means, and electronic image enhancement circuitry.

With reference to FIG. 2, the second imaging apparatus B in one preferred embodiment is a digital radiographic imaging system. Optionally, other imagers which are lower cost, faster, or more readily accessible than the first imager A may also be utilized, e.g. ultrasound, conventional x-ray, obsolete, low resolution, or single plane CT scanners, or the like. An X-ray source 50 projects a three dimensional swath of radiation onto an X-ray detecting array 52. The array 52 in the illustrated embodiment is a rectangular array of CCD devices or other electronic components which convert radiation intensity into corresponding electronic signals. A patient table 54 supports and fixes the region of the patient which had been examined by the first imaging means A between the X-ray source and detector array. Optionally, belts or straps may be utilized to fix the position of the patient relative to the patient table and second imager more securely. In this manner, electronic data representing a shadowgraphic calibration reference image of the region of interest is generated. It is to be appreciated, that the radiation which generates the shadowgraphic image originates at essentially a point source in the X-ray tube 50 and passes along diverging rays between the X-ray source and each element of the detector array 52. Thus, the shadowgraphic image represents shadowgraphic projections along diverging rays through the region of interest. The exact path followed by each ray is readily calculated from the geometry of the second imager apparatus B. In particular, from the distance between the X-ray source 50 and the patient, the distance between the X-ray source 50 and the detector arrays 52, and the dimensions of the detector array, the path which generates each element of the shadowgraphic image is readily calculated.

A shadowgraphic or calibration reference image memory 60 stores the shadowgraphic image data from the detector array 52. A calibration reference image format means 62 formats the data appropriately to produce a man-readable display on a display means 64.

The multi-slice diagnostic image data from the residual storage means 40 is transferred to a three dimensional or multi-slice image memory 32' of substantially the same configuration as the three dimensional or multi-slice image memory of the first imager A. An image format means 36' selects and formats the appropriate data from the image memory to produce a man-readable display on the display means 64 representing the plane and angular orientation selected on a plane and angular orientation selection means 34'. These means function analogously with the correspondingly numbered elements of the first imager.

A projection format means 70 selects the appropriate data from the multi-slice memory 32' to synthesize a shadowgraphic image analogous to the image generated from the data in the shadowgraphic image memory 60. In particular, the projection format means 70 selects data in accordance with the geometry of the second imager B. The selection may be conceptualized by projecting imaginary rays originating at a point the same distance from the three dimensional array of cubic image cells as the X-ray tube 50 is from the patient and which diverge at the same angles as the rays of the second scanner. The data in each of the cells through which one of these rays passes is summed to generate one pixel representing a shadowgraphic projection image from the multi-slice diagnostic data. The plane and orientation selection means 34' is interconnected with the projection format means such that the origin of the rays may be selectively rotated and shifted.

A superimposing means 72 superimposes the shadowgraphic projection diagnostic and calibration reference projection images from the projection format means and from the shadowgraphic image format means 62. The image from the projection format means 70 is adjusted in orientation and position by the plane and angle selection means 34' until at least a region of interest within the images is most accurately superimposed and coincident. If appropriate, a scale adjusting means 74 may adjust the dimensional scale of the image from the projection format means 70. The scale adjustment may be made by linearly adjusting one or more dimensions or by shifting the origin of the converging rays closer or further away from the region of interest. The scale adjusting means and the plane and angle selection means include a scale, position, and angle offset memory 76 for storing the scale, position, and angle selected data at which calibration is completed. Where appropriate, the memory may sum scale, position, and angle data received from other sources. After the calibration is completed, the scale, position, and angle data are fixed in the memory such that the position and orientation selection means may be utilized for calibrations along another axis or to select the orientation of diagnostic images for viewing.

Optionally, an automatic alignment means 78 may be utilized to bring the two images into coincidence. The automatic alignment means may utilize conventional automatic picture focuses techniques or map reading and identification techniques for iteratively adjusting the selected orientation, position, and scale of the diagnostic data projection image until a best match of the images or a selected portion thereof is achieved.

Preferably, the radiation source 50 and detector array 52 of the second imaging means B are rotatable such that a second calibration reference shadowgraphic image is generated through the patient from another angular orientation. For simplicity of mathematical calculation, the calibration reference images are preferably taken through the patient along the orthogonal x and y coordinate axes, such as vertical and horizontal. An angle resolver 80 detects the exact angular position of the X-ray source and detector array which angular position is stored in a memory means 82. The angle memory means 82 is interconnected with the scale, position, and angle offset means to provide a reference orientation of the shadowgraphic calibration reference image from the second imager to define the axis relative to which the position and orientation offset data is relative.

With the X-ray source and detector array in the second position, the two superimposed shadowgraphic images are again brought into alignment. If the X-ray source and detector ray are positioned vertically for the first adjustment, the first adjustment provides the appropriate spatial position and angular orientation offsets relative to the vertical axis. If the X-ray sources and detector array are positioned along a horizontal axis for the second calibration, the second scale, origin, and angular adjustment will provide the appropriate spatial position and angular orientation offsets to adjust the data in the image memory 32' relative to the horizontal axis.

After the calibration adjustment, planes and orientations called up on the plane and orientation selection means 34' have the appropriate angular and spatial offset added thereto by the offset memory 76 such that the image format means 36' selects the planes and orientations in the coordinate system in which the patient is currently disposed. A coordinate superimposing means 84 superimposes dimensions or other coordinate position data on images generated by the diagnostic images.

In one embodiment, the stereostatic surgery means C includes a guide or tube 90 which is mounted on a carriage 92 which may be selectively positioned along the longitudinal axis of the patient table. A longitudinal position fixing means 94 selectively locks the carriage in a selected longitudinal position. A gimbal assembly 96 enables the tube 90 to be rotated in three dimensions and locked in a selected orientation. In this manner, an inner end 98 of the tube may be positioned adjacent a selected origin or point of entry on or near the surface of the patient and the tube can be positioned and locked along any selected axis. Because the patient and the stereotactic surgery means are both fixed relative to the patient table, they are fixed relative to each other.

An invasive surgical instrument 100, such as a biopsy needle, an abcess drainage needle, a radiation implantation probe, an orthopedic pin placement apparatus, a contrast or other medication injection syringe, or the like, is slidably receivable in the tube. An adjustable stop means 102 limits the distance with which the instrument may be inserted into the tube, hence, the depth to which the leading end penetrates the patient. This enables the physician or surgeon to insert the instrument manually into the patient until its leading end is at the selected site. Manual insertion is advantageous in that the physician is provided with tactile feedback as the instrument penetrates different tissue types.

Alternately, an automated insertion guide or robotic arm arrangement may be utilized. In the automated version, the operator inputs the spatial coordinates of the point of entry into the patient on the angle of entry relative to the three axes with an origin and angle selection means 110. A spatial position control means 112 provides control signals to the drive motors for a three arm controller 114 such that the leading end of a third arm 116 is positioned at the selected origin. An angle control means 118 causes the robotic arms to be rotated such that the third arm 116 is in the selected angular orientation. The third arm may again be a tube through which the physician manually inserts the surgical implement. Alternately, the third arm may be the surgical instrument itself and its control motor may again be actuated such that the third arm advances a preselected distance at the set angle to perform the selected surgical function.

Although the first imaging apparatus has been described as a CT scanner, it is to be appreciated that other multi-slice and three dimensional imaging techniques may also be utilized. Other three dimensional imaging techniques include magnetic resonance imaging, emission CT such as positron emission tomography, ultrasound, and composite imaging techniques. Although the second imaging apparatus has been described as a digital radiographic imaging system, it is to be appreciated that other imaging systems may also be utilized, such as ultrasonic, imagers, obsolete low speed CT imagers, and the like. As another alternative, electronic digital shadowgraphic data may be generated by a scanning photodensiometer or the like from a conventional shadowgraphic photographic film image. A photographic shadowgraphic instrument may also be utilized to produce a photographic image which may be laid upon the display means 64 for superimposing calibration purposes.

The invention has been described with reference to the preferred embodiments. Obviously, modifications and alterations will occur to others upon reading and understanding the preceding detailed description. It is intended that the invention be construed as including all such alternations and modifications in so far as they come within the scope of the appended claims or the equivalents thereof.

Having thus described the preferred embodiment, the invention is now claimed to be:

1. A clinical method in which a surgical instrument is precisely positioned relative to an internal region of the subject in advance of an invasive procedure, the method comprising:
   imaging a volume of the subject to locate a structure within the subject precisely and producing three dimensional diagnostic mapping data indicative thereof;
   transferring the subject to a clinical treatment station at which the invasive procedure is to be performed, imaging the patient to relocate the structure within the patient relative to the treatment station by generating a two dimensional calibration reference image through the imaged volume that includes the structure prior to instituting the invasive procedure;
   configuring an analogous two dimensional image from the three dimensional diagnostic mapping data;
   comparing the calibration reference and diagnostic data two dimensional images to determine the relative orientation between the patient and the three dimensional mapping data; and,
   in accordance with the comparing step, moving and orienting the surgical instrument to position the surgical instrument relative to the imaged volume for invasive treatment of the located structure.

2. The method as set forth in claim 1 further including generating a series of planar slice images generated from the mapping data and selecting a point of entry into the subject and a path through the patient for the invasive procedure from the planar slice images.

3. The method as set forth in claim 2 further including at the clinical treatment station prior to the two dimensional calibration reference image generating step, fixing the position of the surgical instrument relative to the subject such that the surgical instrument is constrainable to enter the subject through the selected point of entry and follow the selected path through the subject.

4. The method as set forth in claim 3 further including inserting the surgical instrument through the entrance site and along the selected path of the subject.

5. The method as set forth in claim 4 wherein the instrument insertion step is performed automatically with a robotic arm arrangement which carries the surgical instrument.

6. The method as set forth in claim 1 wherein the step of imaging a volume includes scanning the subject with a computed tomographic scanner and generating a series of planar images from the mapping data.

7. The method as set forth in claim 1 wherein the step of generating a two dimensional calibration reference image includes examining the subject with a digital radiographic imaging apparatus wherein the two dimensional calibration reference image is a calibration reference shadowgraphic projection image and wherein the configuring step includes configuring an analogous projection image from the diagnostic mapping data.

8. The method as set forth in claim 7 wherein the comparing step includes superimposing the calibration reference shadow graphic projection and the analogous diagnostic data projection images in a common display.

9. A clinical method in which an internal region of a subject is precisely located in advance of an invasive procedure, the method comprising:
  imaging a volume of the subject at a first location and producing three-dimensional diagnostic mapping data indicative thereof;
  at a second location in which the invasive procedure is to be performed, imaging the subject to generate a two dimensional calibration reference image through a region of interest prior to instituting the invasive procedure, the step of generating a two dimensional calibration reference image including examining the subject with a digital radiographic imaging apparatus such that the two dimensional calibration reference image is a calibration reference shadowgraphic projection image;
  projecting a projection image from the three-dimensional diagnostic mapping data which projection image is analogous to the two dimensional calibration reference image;
  comparing the calibration reference image and the analogous projection image; and,
  adjusting spatial position and angular orientation through which the mapping data is projected into the analogous projection image until a selected portion of the analogous projection image most accurately matches a corresponding selected portion of the calibration reference image, whereby the mapping data is brought into at least partial registration with the actual, current position of the subject.

10. In a clinical procedure wherein an internal region of the subject is subjected to an invasive procedure, precisely locating and mapping said internal region in advance of the procedure comprising the steps of:
  conducting a series of planar scans of the subject and obtaining three-dimensional electronic mapping data indicative of internal structure of at least said internal region of the subject from the scans;
  generating man-readable images from the mapping data and identifying the internal region to be treated by the invasive procedure from the man-readable images;
  selecting a point of entry into the subject and a path through the subject from the man-readable images;
  fixing the position of the subject relative to a clinical station where the invasive procedure is to be performed;
  performing a non-invasive imaging of the patient to produce a first calibration reference image representing a two dimensional shadowgraph of a least a portion of the subject along a first direction which includes said internal region;
  generating analogous shadowgraphic projection image from the three-dimensional electronic mapping data which analogous shadowgraphic projection image represents a projection through the three-dimensional electronic mapping data along a calibration direction that substantially matches the first direction;
  comparing the calibration reference and three-dimensional electronic mapping shadowgraphic images to obtain an indication of the location of said internal region in relation to the clinical station;
  positioning an invasive instrument guide to aim a surgical instrument to enter the subject at the selected point of entry and follow the selected path; and,
  producing a second calibration reference image of the guide and the subject to check to guide positioning.

11. An apparatus for performing an invasive surgical procedure on a subject, the apparatus comprising:
  scanning means for scanning at least a selected region of the subject and generating an electronic mapping data representing a three dimensional region of the subject;
  an image memory means for storing the mapping data;
  a display means for displaying man-readable diagnostic images reconstructed from the mapping data in the image memory, which diagnostic images represent slices through the region of interest;
  an imaging means for generating and storing electronic data representative of a two dimensional reference image through the region of interest, the imaging means being operatively connected with the display means for displaying a man-readable two dimensional reference image from the stored data;
  a reformatting means for reformatting the mapping data from the image memory into a reformatted diagnostic image of the format of the reference image from the imaging means;
  an adjusting means for adjusting spatial position and angular orientation with which the reformatting means reformats the mapping data such that the reformatted image more closely matches the reference image; and,
  a surgical instrument positioning means for positioning a surgical instrument relative to the patient to direct the surgical instrument to penetrate the patient at an entrance point selected from the diagnostic images, after generation of the images, and proceed along a path selected from the diagnostic images.

12. The apparatus as set forth in claim 11 further including a portable electronic data storage means which is operatively connected with the image memory means for receiving and storing the mapping data therefrom and which means is transportable to another image memory for transferring the mapping data thereto.

13. The apparatus as set forth in claim 11 wherein the imaging means is a digital radiographic imaging means and the reference image is a shadowgraphic projection image.

14. The apparatus as set forth in claim 13 wherein the reformatting means includes means for reformatting a shadowgraphic projection from the mapping data which is analogous to the reference shadowgraphic projection images of the digital radiographic imaging means such that the reformatted image represents a shadowgraphic projection and wherein the adjusting means adjusts the spatial position and angular orientation with which the projections are reformatted, whereby the orientation and position of the reformatted shadowgraphic image is adjustable until it most accurately matches the reference shadowgraphic image.

15. The apparatus as set forth in claim 14 further including a superimposing means for combining the reformatted and reference shadowgraphic images to facilitate comparison thereof.

16. The apparatus as set forth in claim 11 wherein the scanning means is a computerized tomographic scanner.

17. The apparatus as set forth in claim 11 wherein the surgical instrument positioning means includes an arm arrangement and a control means for robotically controlling the arm arrangement.

\* \* \* \* \*